(12) United States Patent
Ye et al.

(10) Patent No.: US 11,414,427 B2
(45) Date of Patent: Aug. 16, 2022

(54) SOLID FORMS OF STEMOSPIRONINE AND ITS SALTS

(71) Applicants: Yang Ye, Shanghai (CN); Sheng Yao, Shanghai (CN); Hui-Yin Li, Hockessen, DE (US); Qun Li, Newark, DE (US)

(72) Inventors: Yang Ye, Shanghai (CN); Sheng Yao, Shanghai (CN); Hui-Yin Li, Hockessen, DE (US); Qun Li, Newark, DE (US)

( * ) Notice: Subject to any disclaimer, the term of this patent is extended or adjusted under 35 U.S.C. 154(b) by 0 days.

(21) Appl. No.: 16/646,694

(22) PCT Filed: Sep. 7, 2018

(86) PCT No.: PCT/US2018/049851
§ 371 (c)(1),
(2) Date: Mar. 12, 2020

(87) PCT Pub. No.: WO2019/055294
PCT Pub. Date: Mar. 21, 2019

(65) Prior Publication Data
US 2020/0407368 A1  Dec. 31, 2020

Related U.S. Application Data

(60) Provisional application No. 62/606,161, filed on Sep. 12, 2017.

(51) Int. Cl.
| C07D 491/20 | (2006.01) |
| C07C 59/255 | (2006.01) |
| C07C 309/04 | (2006.01) |
| C07C 309/05 | (2006.01) |
| C07C 309/19 | (2006.01) |

(52) U.S. Cl.
CPC .......... C07D 491/20 (2013.01); C07C 59/255 (2013.01); C07C 309/04 (2013.01); C07C 309/05 (2013.01); C07C 309/19 (2013.01); C07B 2200/13 (2013.01)

(58) Field of Classification Search
CPC .................................................. C07D 491/20
USPC ..................................................... 514/212.02
See application file for complete search history.

(56) References Cited

U.S. PATENT DOCUMENTS

| 2003/0229071 A1* | 12/2003 | Lin ........................ A61P 11/14 514/214.01 |
| 2007/0060564 A1* | 3/2007 | But ........................ A61P 11/14 514/212.02 |
| 2009/0176818 A1 | 7/2009 | Izumimoto et al. |

FOREIGN PATENT DOCUMENTS

| CN | 104138381 | 11/2014 |
| WO | 2009/046635 | 4/2009 |

OTHER PUBLICATIONS

Suzuki, Yakugaku Zasshi (1931), 51, 419-29.*
Suzuki, Yakugaku Zasshi (1934)54, 561-6, Abstracts 101-4.*
Sakata, Agricultural and Biological Chemistry (1978), 42(2), 457-63.*
Bardaji, Org. Lett., vol. 14, No. 18, 2012, 4854-4857.*
Wiedmann, Asian journal of pharmaceutical sciences 11 (2016) 722-734.*
Sakata et al., "Stemospironine, a New Insecticidal Alkaloid of *Stemona japonica* Miq. Isolation, Structural Determination and Activity", Agric. Biol. Chem., 1978, vol. 42, No. 2, pp. 457-463.
Bastin et al., "Salt Selection and Optimisation Procedures for Pharmaceutical New Chemical Entities", Organic Process Research & Development, 2000, vol. 4, pp. 427-435.

(Continued)

*Primary Examiner* — Nizal S Chandrakumar
(74) *Attorney, Agent, or Firm* — Wenderoth, Lind & Ponack, L.L.P.

(57) ABSTRACT

Disclosed are stemospironine salts of Formula 1: wherein HX represents HCl, HBr, L-tartaric acid, D-tartaric acid, sulfuric acid, (+)-(1S)-10-camphorsulfonic acid, ethanesulfonic acid and ethane-1,2-disulfonic acid. This invention also provides crystalline polymorph forms of the compound of Formula 1 wherein HX is HCl, stemospironine hydrochloride. This invention also provides a new crystalline form of the compound of Formula 2, stemospironine free base: Also disclosed are compositions containing one or more compounds of Formula 1, methods for controlling cough comprising administering a therapeutically effective amount of a compound of Formula 1, and methods for preparing compounds of Formula 1. Also disclosed is a method for preparing crystalline stemospironine hydrochloride polymorph Form II from stemospironine hydrochloride polymorph Form I.

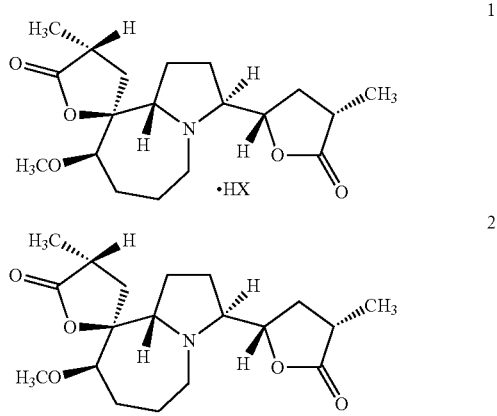

20 Claims, 10 Drawing Sheets

(56) References Cited

OTHER PUBLICATIONS

Partial Supplementary European Search Report dated Apr. 14, 2021 in corresponding European Patent Application No. 18856013.0.
Fukaya et al., "Absolute Structures of Stemona-Lactam S and Tuberostemospiroline, Alkaloids from *Stemona tuberosa*", Chem. Pharm. Bull., 2013, vol. 61, No. 10, pp. 1085-1089.
Ye et al., "Alkaloids of *Stemona japonica*", Phytochemistry, 1994, vol. 37, No. 4, pp. 1205-1208.
Lindsay, K. B., "The asymmetric synthesis of polyfunctional pyrrolidine alkaloids and their analogues", University of Wollongong Theses Collection, University of Wollongong, 2003, pp. 1-75, 94 total pages.
Pilli et al., "The chemistry of *Stemona* alkaloids: An update", Nat. Prod. Rep., 2010, vol. 27, pp. 1908-1937.
International Search Report dated Oct. 24, 2018 in International (PCT) Application No. PCT/US18/49851.
Extended European Search Report dated Aug. 24, 2021, in corresponding European Patent Application No. 18856013.0.
Mino R. Caira, "Crystalline Polymorphism of Organic Compounds", Topics in Current Chemistry, 1998, vol. 198, pp. 163-208.

\* cited by examiner

SOLID FORMS OF STEMOSPIRONINE AND ITS SALTS

FIELD OF THE INVENTION

This invention relates to certain solid forms of stemospironine and its salts, certain polymorph forms thereof and compositions, methods of their use as therapeutic agents, and methods for their preparation.

BACKGROUND OF THE INVENTION

The roots and rhizomes of the plant family Stemonacae have provided a rich source of structurally novel polycyclic alkaloids referred to as Stemona alkaloids. Initial interest in these substances stemmed from the use of plant materials in herbal teas used in Chinese folk medicine. The use of one such Stemona alkaloid, stemospironine, as an antitussive is disclosed in PCT Patent Publication WO 2009/046635.

There is a continuing need for new salts and polymorphs of stemospironine having properties that can contribute to their usefulness as pharmaceuticals, such as improved solubility properties to optimize bioavailability on therapeutic administration, improved taste characteristics, etc.

SUMMARY OF THE INVENTION

This invention is directed to stemospironine salts of Formula 1:

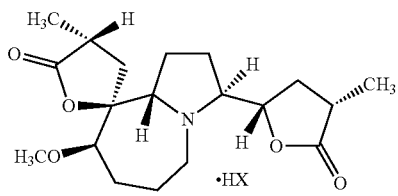

wherein HX represents hydrogen chloride, hydrogen bromide, L-tartaric acid, D-tartaric acid, sulfuric acid, (+)-(1S)-10-camphorsulfonic acid, ethanesulfonic acid and ethane-1,2-disulfonic acid. Each crystalline salt is characterized by peaks appearing in its X-ray powder diffraction (XRPD) pattern.

This invention also provides crystalline polymorph forms of the compound of Formula 1 wherein HX is hydrogen chloride, i.e. stemospironine hydrochloride. Each polymorph form is characterized by the peaks appearing in its X-ray powder diffraction (XRPD) pattern.

This invention also provides a new crystalline form of the compound of Formula 2, i.e. stemospironine free base:

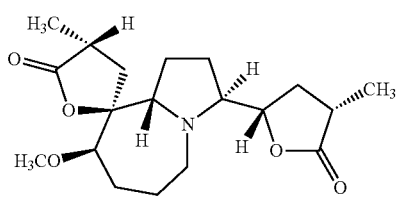

The crystalline form is characterized by the peaks appearing in its X-ray powder diffraction (XRPD) pattern.

This invention also relates to a pharmaceutical composition comprising one or more compounds of Formula 1 (i.e. in a therapeutically effective amount) and a pharmaceutically acceptable carrier.

This invention further relates to a method of controlling cough, i.e. as an antitussive agent, comprising administering to human a therapeutically effective amount of a compound of Formula 1 (e.g. as a composition described herein).

This invention also provides methods for the preparation of salts of Formula 1.

This invention also provides a method for the preparation of crystalline polymorph forms of Compound 1 wherein X is hydrogen chloride, i.e. stemospironine hydrochloride.

This invention also provides a method for the preparation of a crystalline form of a compound of Formula 2, stemospironine free base.

DETAILED DESCRIPTION OF THE INVENTION

Figure 1:
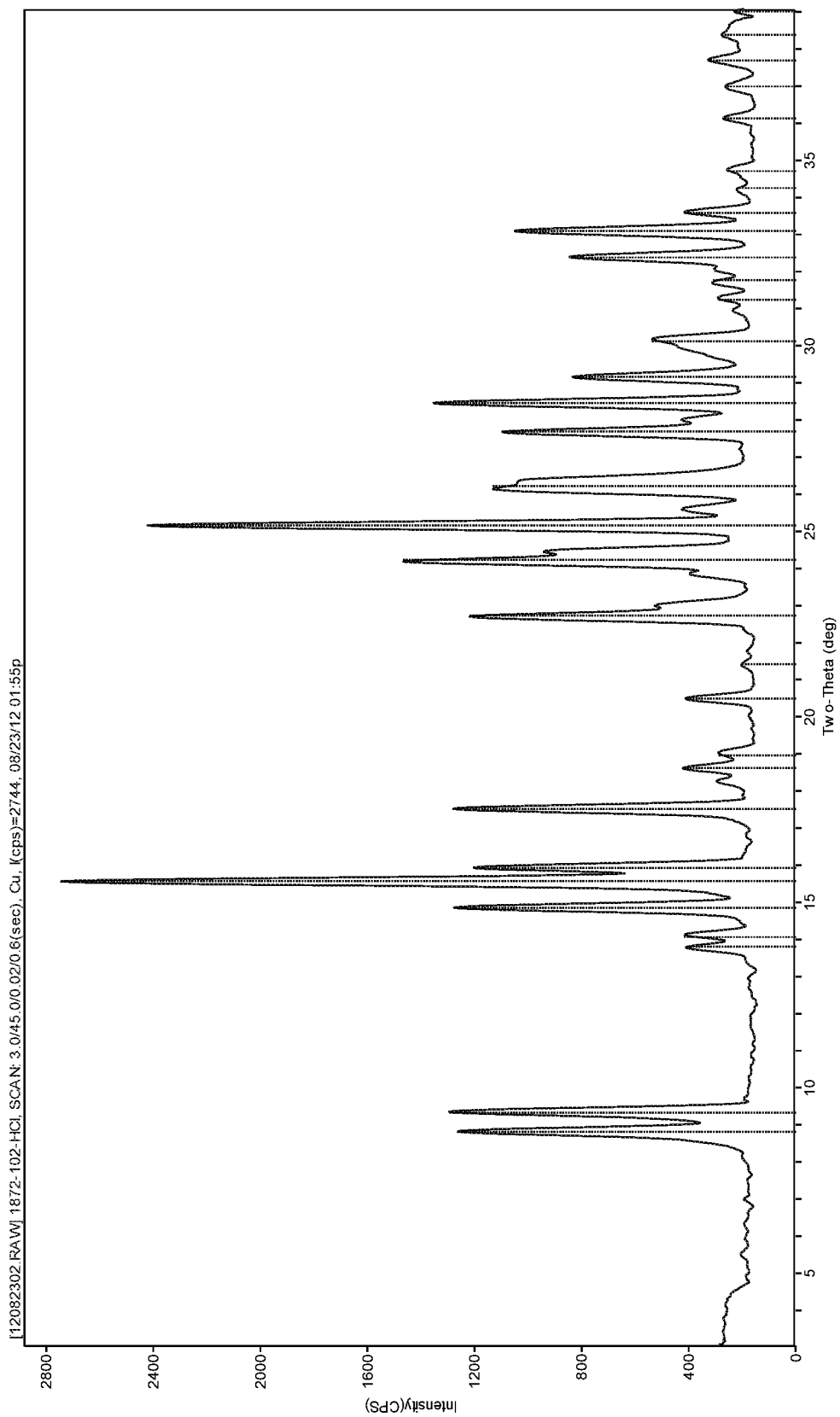
FIG. 1 shows a characteristic X-ray powder diffraction pattern of crystalline polymorph Form I of the 1:1 hydrochloric acid salt of stemospironine.

As used herein, the phrase "pharmaceutically acceptable" refers to those compounds, materials, compositions, carriers and/or dosage forms which are suitable for use in contact with the tissues of human beings and excessive toxicity, irritation, allergic response, or other problems or complications, commensurate with a reasonable benefit/risk ratio.

As used herein, the term "effective amount of" refers to an amount of a compound, or a combination of compounds, of the present invention effective when administered alone or in combination as an antitussive agent.

The term crystalline "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph can exhibit beneficial effects (e.g., suitability for preparation of useful formulations, improved solubility, etc.), relative to another polymorph or a mixture of polymorphs of the same compound. Preparation and isolation of a particular polymorph of a compound can be achieved by methods known to those skilled in the art including, for example, crystallization using selected solvents and temperatures.

Embodiments of the present invention as described in the Summary of the Invention include:

Embodiment 1. The salt of Formula I described in the Summary of the Invention in crystalline form.

Embodiment 2. The salt of Embodiment 1 wherein HX is hydrogen chloride, in the form of a polymorph Form I that exhibits an X-ray powder diffraction pattern as exemplified in FIG. 1.

Embodiment 3. The salt of Embodiment 1 wherein HX is hydrogen chloride, in the form of a polymorph Form I that exhibits an X-ray powder diffraction pattern having characteristic peaks, expressed in degrees 2θ, as shown in Table 1.

Embodiment 4. The salt of Embodiment 1 wherein HX is hydrogen chloride, in the form of a polymorph Form II that exhibits an X-ray powder diffraction pattern as exemplified in FIG. 2.

Embodiment 5. The salt of Embodiment 1 wherein HX is hydrogen chloride, in the form of a polymorph Form II that exhibits an X-ray powder diffraction pattern having characteristic peaks, expressed in degrees 2θ, as shown in Table 2.

Embodiment 6. The salt of Embodiment 1 wherein HX is hydrogen bromide, that exhibits an X-ray powder diffraction pattern as exemplified in FIG. 3.

Embodiment 7. The salt of Embodiment 1 wherein HX is hydrogen bromide, that exhibits an X-ray powder diffraction pattern having characteristic peaks, expressed in degrees 2θ, as shown in Table 3.

Embodiment 8. The salt of Embodiment 1 wherein HX is L-tartaric acid, that exhibits an X-ray powder diffraction pattern as exemplified in FIG. 4.

Embodiment 9. The salt of Embodiment 1 wherein HX is L-tartaric acid, that exhibits an X-ray powder diffraction pattern having characteristic peaks, expressed in degrees 2θ, as shown in Table 4.

Embodiment 10. The salt of Embodiment 1 wherein HX is D-tartaric acid that exhibits an X-ray powder diffraction pattern as exemplified in FIG. 5.

Embodiment 11. The salt of Embodiment 1 wherein HX is D-tartaric acid that exhibits an X-ray powder diffraction pattern having characteristic peaks, expressed in degrees 2θ, as shown in Table 5.

Embodiment 12. The salt of Embodiment 1 wherein HX is sulfuric acid, that exhibits an X-ray powder diffraction pattern as exemplified in FIG. 6.

Embodiment 13. The salt of Embodiment 1 wherein HX is sulfuric acid, that exhibits an X-ray powder diffraction pattern having characteristic peaks, expressed in degrees 2θ, as shown in Table 6.

Embodiment 14. The salt of Embodiment 1 wherein HX is (+)-(1S)-10-camphorsulfonic acid, that exhibits an X-ray powder diffraction pattern as exemplified in FIG. 7.

Embodiment 15. The salt of Embodiment 1 wherein HX is (+)-(1S)-10-camphorsulfonic acid, that exhibits an X-ray powder diffraction pattern having characteristic peaks, expressed in degrees 2θ, as shown in Table 7.

Embodiment 16. The salt of Embodiment 1 wherein HX is ethanesulfonic acid, that exhibits an X-ray powder diffraction pattern as exemplified in FIG. 8.

Embodiment 17. The salt of Embodiment 1 wherein HX is ethanesulfonic acid, that exhibits an X-ray powder diffraction pattern having characteristic peaks, expressed in degrees 2θ, as shown in Table 8.

Embodiment 18. The salt of Embodiment 1 wherein HX is 1,2-ethanedisulfonic acid, that exhibits an X-ray powder diffraction pattern as exemplified in FIG. 9.

Embodiment 17. The salt of Embodiment 1 wherein HX is 1,2-ethanedisulfonic acid, that exhibits an X-ray powder diffraction pattern having characteristic peaks, expressed in degrees 2θ, as shown in Table 9.

Embodiment 18. A crystalline form of the compound of Formula 2, i.e. stemospironine free base, that exhibits an X-ray powder diffraction pattern as exemplified in FIG. 10.

Embodiment 19. A crystalline form of the compound of Formula 2, i.e. stemospironine free base, that exhibits an X-ray powder diffraction pattern having characteristic peaks, expressed in degrees 2θ, as shown in Table 10.

This invention provides a pharmaceutical composition comprising one or more compounds of Formula 1 and a pharmaceutically acceptable carrier. Of note as embodiments of such compositions are compositions comprising a compound corresponding to any of the embodiments described above.

This invention provides a method of controlling cough comprising administering to a human a therapeutically effective amount of a compound of Formula 1. Of note as embodiments of such methods are methods comprising applying a therapeutically effective amount of a compound corresponding to any of the embodiments described above. Of particular note are embodiments where compounds are applied as compositions of this invention. Also of particular note are embodiments where compounds are administered orally.

The present invention further discloses a method for preparing crystalline stemosporinine salts of Formula 1 from stemosporinine, a compound of Formula 2, and an acid HX, comprising:

A) dissolving the compound of Formula 2, stemospironne, in a suitable first solvent to form a solution A;

B) adding an acid HX, optionally dissolved in a sutiable second solvent, to solution A to form a reaction mixture;

C) optionally adding a third solvent; and

D) separating the resulting solid, i.e. a compound of Formula 1, from the reaction mixture.

The first and second solvents are independently selected from the group consisting of water, methanol, ethanol, isopropanol and acetonitrile.

The third solvent is independently selected from the group consisting of methyl tert-butyl ether, heptane and hexane.

The acid HX is selected from the group consisting of hydrogen chloride, hydrogen bromide, L-tartaric acid, D-tartaric acid, sulfuric acid, (+)-(1S)-10-camphorsulfonic acid, ethanesulfonic acid and ethane-1,2-disulfonic acid.

The present invention further discloses a method for preparing crystalline stemospironne hydrochloride polymorph Form II comprising:

A) dissolving crystalline stemospironne hydrochloride polymorph Form I in acetonitrile at 50° C.;

B) evaporating said acetonitrile solution at at 50° C.;

C) recovering crystalline stemospironne hydrochloride polymorph Form II; and

D) drying said stemospironne hydrochloride polymorph Form II.

The polymorph salts of the present invention (i.e. a compound of Formula 1 wherein HX is hydrogen chloride) may be in a non-solvated form or a solvated form, in particular in a hydrated form or an alcoholated form.

The polymorph salts of the present invention (i.e. a compound of Formula 1 wherein HX is hydrogen chloride) may be in an amorphous form or in various crystalline forms thereof, or in a form of a mixture of these forms.

Polymorph forms of the present invention are characterized by the peaks appearing in the X-ray powder diffraction (XRPD) pattern. The XRPD patterns of the polymorphs of this invention were measured by a Rigaku Miniflex X-ray Powder Diffractometer (XRPD) instrument.

X-ray radiation is from Copper Cu at 1.054056 Å with $K_\beta$ filter. X-ray power is 30 KV, 15 mA. Sample powder is dispersed on a zero-background sample holder. General measurement conditions are: start angle −3; stop angle −45; scan speed −2 deg/min.

Example 1a

Preparation of Polymorph Form I of the 1:1 Hydrochloric Acid Salt of Stemospironine A stirred suspension of stemospironine (2.24 g, 6.37 mmol) in methanol (15 mL) was heated to 55° C. over 15 min. To the resulting solution was added 1.0 M hydrogen chloride in isopropanol (7.33 mL, 7.33 mmol, 1.15 equiv) followed by methyl tert-butyl ether, and the resulting slurry was stirred at room temperature for 8 h. The resulting solid was filtered, washed with methyl tert-butyl ether (10 mL) and dried under reduced pressure at 20-21° C. to afford the title compound (1.32 g, 92.6%) as a crystalline solid which was characterized by XRPD. FIG. 1 shows a characteristic X-ray powder diffraction (XRPD) pattern of polymorph Form 1 of the 1:1 hydrochloric acid salt of stemospironine. Characteristic peaks, expressed in degrees 2θ, are listed in Table 1.

TABLE 1

| Angle 2θ [°] | Relative Intensity (%) |
| --- | --- |
| 8.818 | 42.1 |
| 9.333 | 43.2 |
| 13.806 | 9.3 |
| 14.065 | 9 |
| 14.853 | 40.6 |
| 15.568 | 100 |
| 15.931 | 38.9 |
| 17.514 | 42.7 |
| 18.621 | 9.6 |
| 18.966 | 4.8 |
| 20.494 | 10 |
| 22.731 | 41.2 |
| 24.228 | 48.7 |
| 25.159 | 85.2 |
| 26.217 | 35.3 |
| 27.697 | 33.9 |
| 28.455 | 44.2 |
| 29.167 | 23.9 |
| 30.124 | 13.4 |
| 32.384 | 25.4 |
| 33.101 | 33.8 |
| 33.584 | 9.3 |

Example 1b

Figure 2:
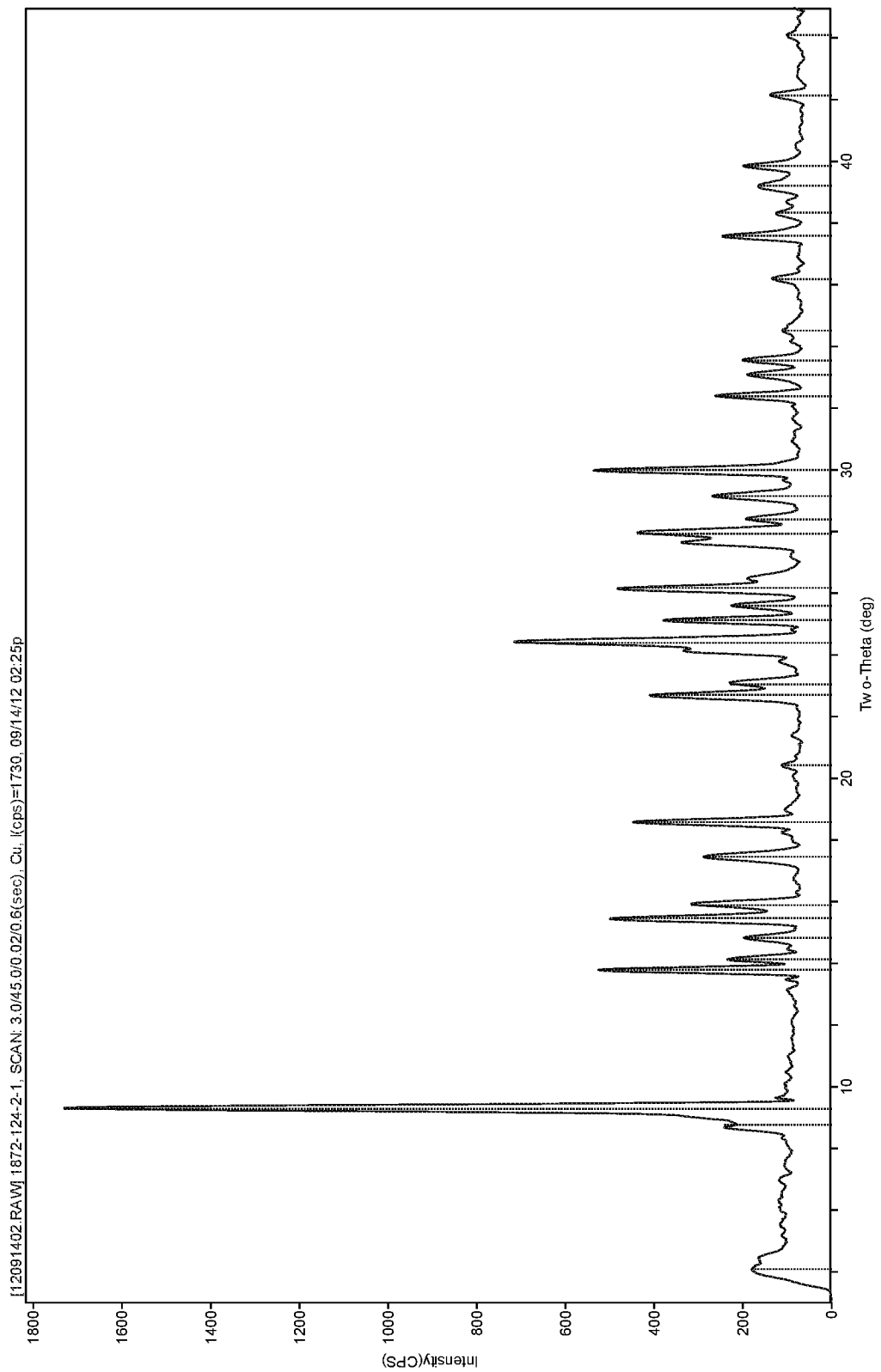
FIG. 2 shows a characteristic X-ray powder diffraction pattern of crystalline polymorph Form II of the 1:1 hydrochloric acid salt of stemospironine.

Preparation of Polymorph Form II of the 1:1 Hydrochloric Acid Salt of Stemospironine Evaporation of an acetonitrile solution of the polymorph Form I of the 1:1 hydrochloric acid salt of stemospironine (prepared as described in Example 1a) at 50° C. afforded the title compound which was characterized by XRPD. FIG. 2 shows a characteristic X-ray powder diffraction (XRPD) pattern of polymorph Form II of the 1:1 hydrochloric acid salt of stemosporinine. Characteristic peaks, expressed in degrees 2θ, are listed in Table 2.

TABLE 2

| Angle 2θ [°] | Relative Intensity (%) |
| --- | --- |
| 8.772 | 8.4 |
| 9.294 | 100 |
| 13.795 | 26.7 |
| 14.137 | 8.3 |
| 14.825 | 6.6 |
| 15.47 | 25.6 |
| 15.889 | 14.7 |
| 17.456 | 13.3 |
| 18.579 | 23.2 |
| 22.702 | 20.8 |
| 23.047 | 9.5 |
| 24.39 | 39.2 |
| 25.128 | 18.1 |
| 25.593 | 8.5 |
| 26.174 | 24.6 |
| 27.929 | 22.4 |
| 28.389 | 6.9 |
| 29.153 | 11.3 |
| 29.993 | 28 |
| 32.39 | 11.9 |
| 33.083 | 7.4 |
| 33.55 | 8.1 |
| 36.186 | 4.2 |
| 37.594 | 11 |
| 39.215 | 5.3 |
| 39.851 | 7.8 |
| 42.139 | 4.7 |

Example 2

Preparation of the 1:1 Hydrobromic Acid Salt of Stemospironine

Figure 3:
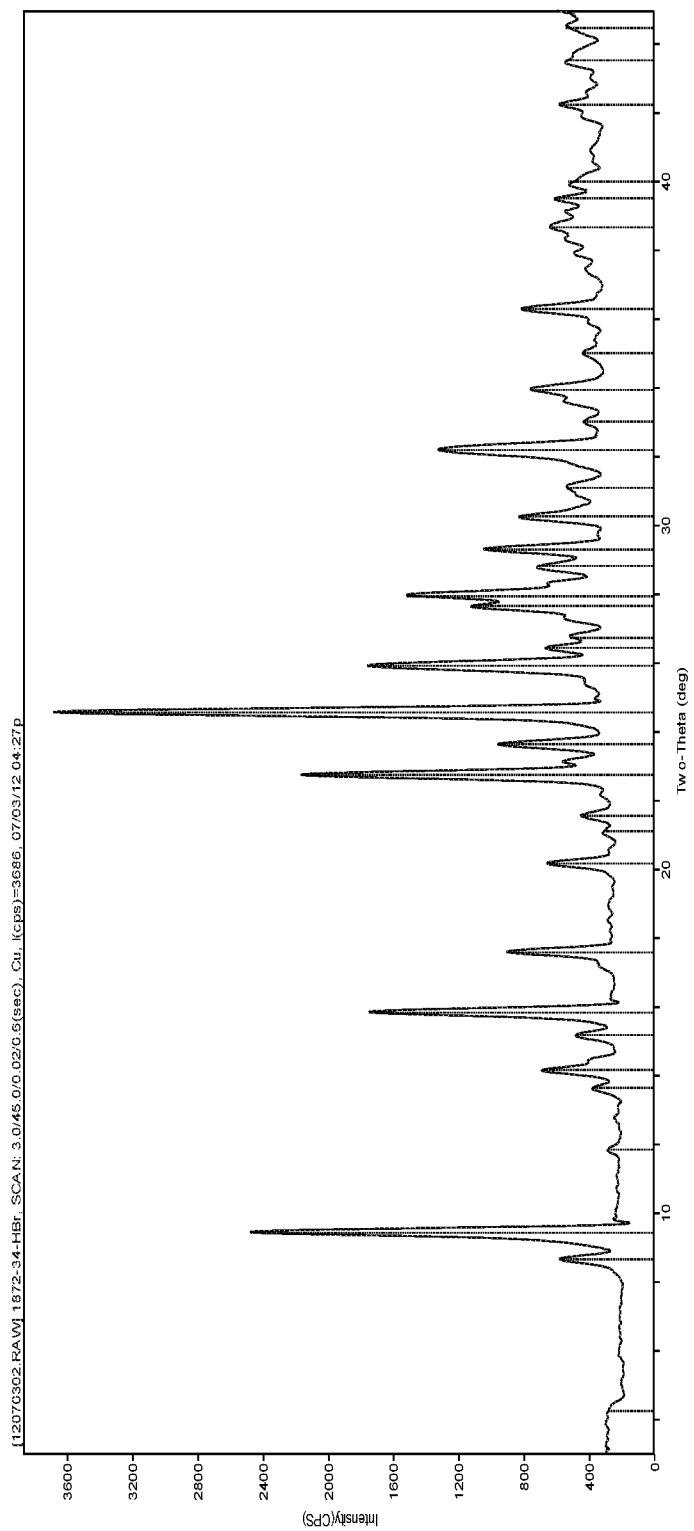
FIG. 3 shows a characteristic pattern of crystalline 1:1 hydrobromic acid salt of stemospironine.

Using the method of Example 1a, the title compound (96.3%) was obtained as a crystalline solid which was characterized by XRPD. FIG. 3 shows a characteristic X-ray powder diffraction (XRPD) pattern of stemospironine monohydrobromide. Characteristic peaks, expressed in degrees 2θ, are listed in Table 3.

TABLE 3

| Angle 2θ [°] | Relative Intensity (%) |
| --- | --- |
| 8.664 | 10.9 |
| 9.434 | 67.3 |
| 13.648 | 4.7 |
| 14.179 | 13.8 |
| 15.188 | 7.1 |
| 15.84 | 45 |
| 17.588 | 19.4 |
| 20.174 | 12.4 |
| 21.559 | 5.6 |
| 22.755 | 54.7 |
| 23.644 | 17.8 |
| 24.567 | 100 |
| 25.924 | 42.1 |
| 26.445 | 8.8 |

TABLE 3-continued

| Angle 2θ [°] | Relative Intensity (%) |
| --- | --- |
| 27.666 | 22.4 |
| 27.949 | 33.5 |
| 28.827 | 9.2 |
| 29.306 | 20.1 |
| 30.268 | 14.1 |
| 31.1 | 5.1 |
| 32.198 | 29.4 |
| 33.95 | 13 |
| 36.298 | 14.6 |
| 42.236 | 7.3 |

Example 3

Preparation of the 1:1 L-Tartaric Acid Salt of Stemospironine

Figure 4:
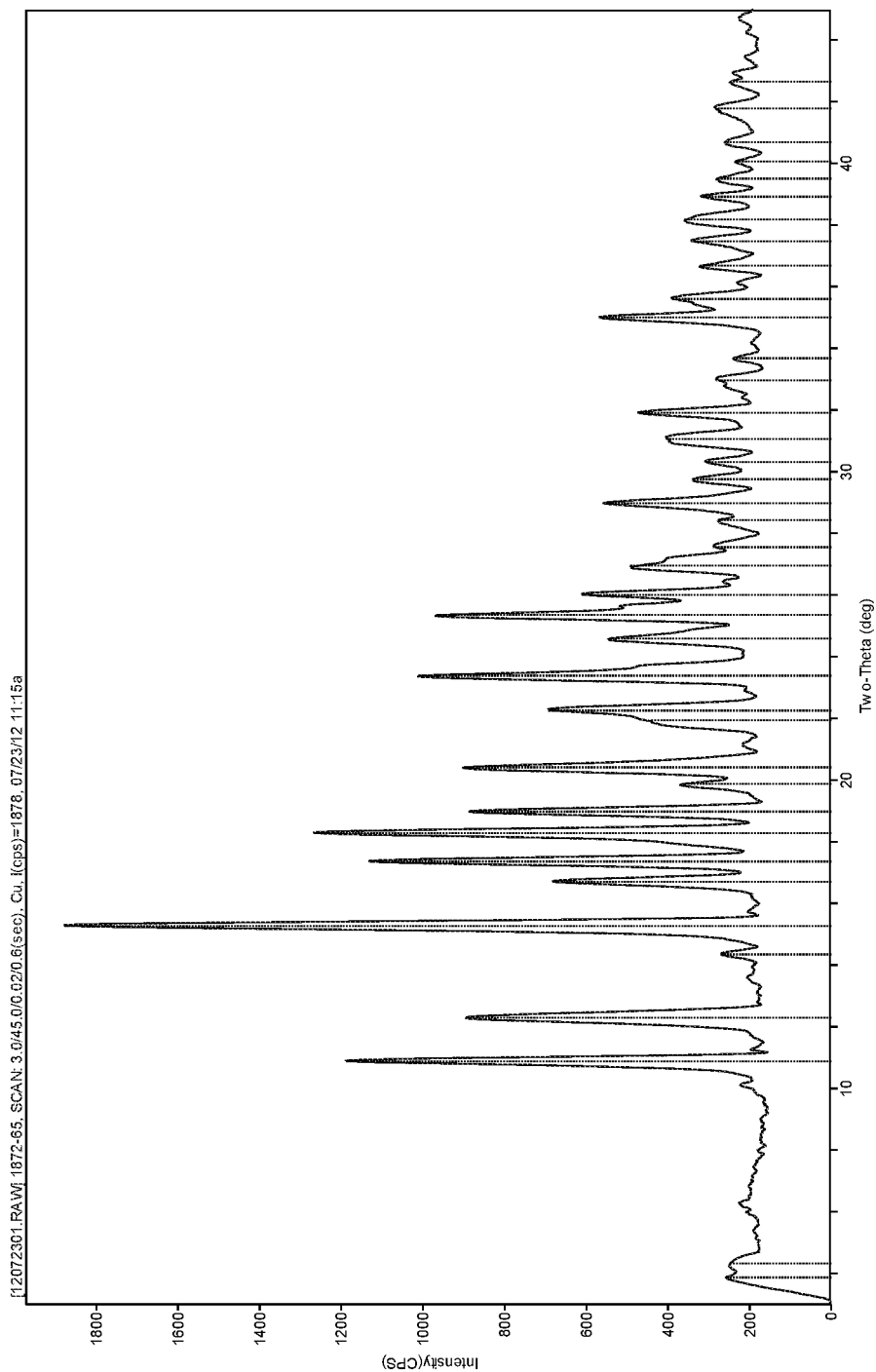
FIG. 4 shows a characteristic X-ray powder diffraction pattern of crystalline 1:1 L-tartaric acid salt of stemospironine.

To a stirred solution of stemosporinnne (395 mg, 1.14 mmol) and L-tartaric acid (195 mg, 1.29 mmol, 1.15 equiv) in acetonitrile (3 mL) and methanol (1 mL) was added methyl tert-butyl ether (5 mL), and the resulting slurry was stirred at room temperature for 5 h. The resulting solid was filtered, washed with methyl tert-butyl ether (1.5 mL) and dried under reduced pressure at 20-21° C. to afford the title compound (553 mg, 98.0%) as a crystalline solid which was characterized by XRPD. FIG. 4 shows a characteristic X-ray powder diffraction (XRPD) pattern of the 1:1 L-tartaric acid salt of stemospironine. Characteristic peaks, expressed in degrees 2θ, are listed in Table 4.

TABLE 4

| Angle 2θ [°] | Relative Intensity (%) |
| --- | --- |
| 10.873 | 59.5 |
| 12.296 | 42.4 |
| 14.346 | 5 |
| 15.269 | 100 |
| 16.703 | 28.5 |
| 17.363 | 53.7 |
| 18.277 | 62.5 |
| 18.979 | 40.6 |
| 19.871 | 10.6 |
| 20.409 | 42.3 |
| 22.259 | 29.8 |
| 23.388 | 47.9 |
| 24.589 | 18.2 |
| 25.362 | 42.2 |
| 26.002 | 21.6 |
| 26.96 | 15.9 |
| 27.551 | 5.5 |
| 28.973 | 21.3 |
| 29.758 | 8.1 |
| 30.31 | 6.3 |
| 31.063 | 11.2 |
| 31.914 | 15.4 |
| 35.009 | 22.4 |
| 35.603 | 12 |
| 36.677 | 8 |
| 37.476 | 8.3 |
| 38.172 | 9.2 |
| 38.918 | 6.8 |
| 39.497 | 5.1 |
| 40.682 | 4.5 |
| 41.781 | 6 |

Example 4

Preparation of the 1:1 D-Tartaric Acid Salt of Stemospironine

Figure 5:
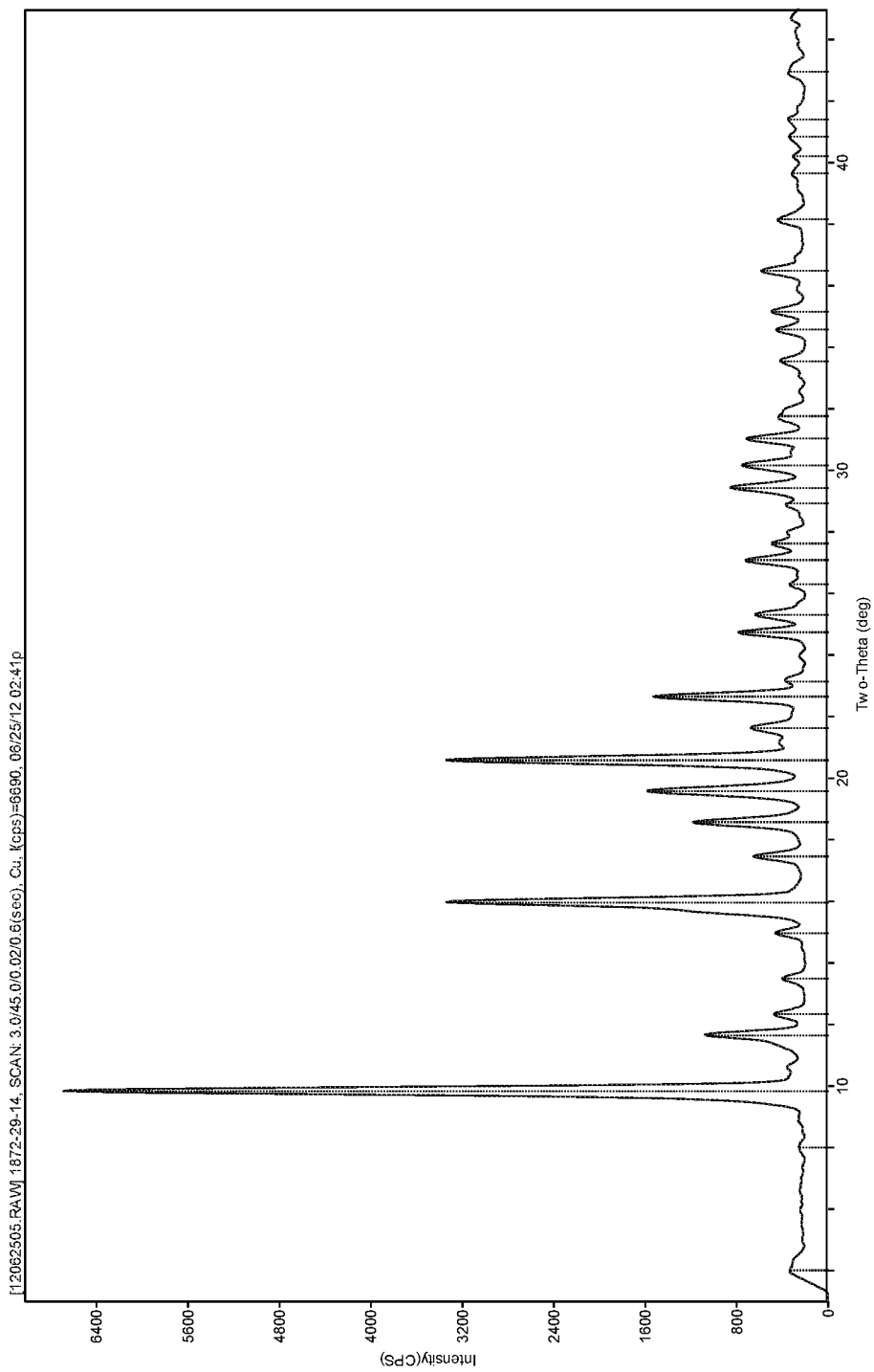
FIG. 5 shows a characteristic X-ray powder diffraction pattern of crystalline 1:1 D-tartaric acid salt of stemospironine.

Using the method of Example 3 stemosporinnne and D-tartaric acid yielded the title compound as a crystalline solid which was characterized by XRPD. FIG. 5 shows a characteristic X-ray powder diffraction (XRPD) pattern of the 1:1 D-tartaric acid salt of stemospironine. Characteristic peaks, expressed in degrees 2θ, are listed in Table 5.

TABLE 5

| Angle 2θ [°] | Relative Intensity (%) |
| --- | --- |
| 9.834 | 100 |
| 11.641 | 12.9 |
| 12.342 | 3.5 |
| 13.487 | 3.1 |
| 14.967 | 3.3 |
| 15.957 | 48.1 |
| 17.457 | 6.3 |
| 18.57 | 14.4 |
| 19.583 | 20.2 |
| 20.583 | 46.4 |
| 21.63 | 5 |
| 22.655 | 19.4 |
| 24.738 | 8.8 |
| 25.312 | 6.8 |
| 27.084 | 7.2 |
| 27.63 | 4 |
| 29.432 | 8.9 |
| 30.163 | 7 |
| 31.035 | 6.6 |
| 34.582 | 3.8 |
| 35.16 | 4.3 |
| 36.489 | 5.6 |
| 38.156 | 3.5 |
| 40.849 | 1.5 |
| 41.401 | 1.9 |

Example 5

Preparation of the 1:1 Sulfuric Acid Salt of Stemospironine

Figure 6:
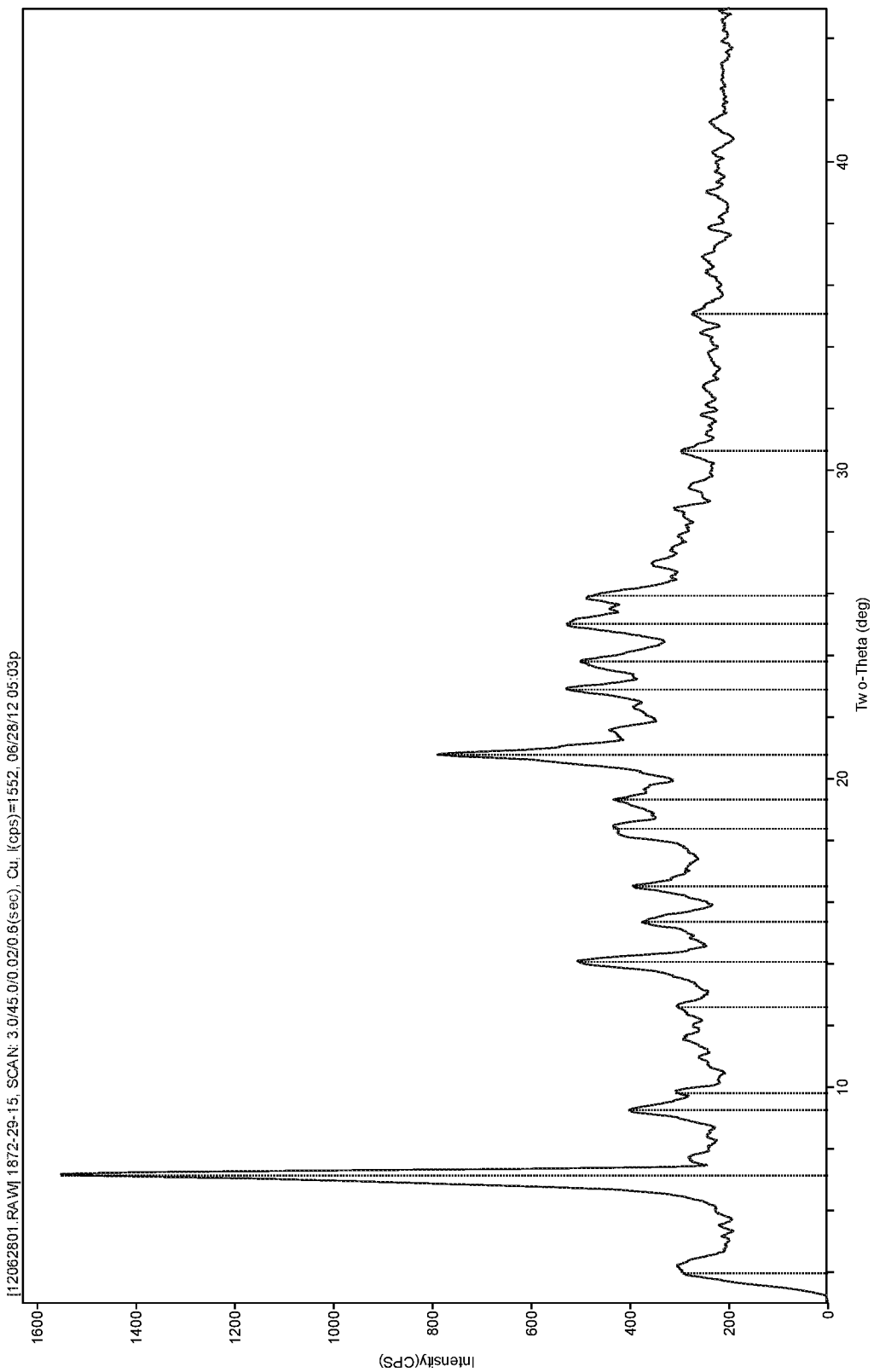
FIG. 6 shows a characteristic X-ray powder diffraction pattern of crystalline 1:1 sulfuric acid salt of stemospironine.

Using the method of Example 3 stemosporinnne and sulfuric acid yielded the title compound as a crystalline solid which was characterized by XRPD. FIG. 6 shows a characteristic X-ray powder diffraction (XRPD) pattern of the 1:1 sulfuric acid salt of stemospironine. Characteristic peaks, expressed in degrees 2θ, are listed in Table 6.

TABLE 6

| Angle 2θ [°] | Relative Intensity (%) |
| --- | --- |
| 7.13 | 100 |
| 9.257 | 13.4 |
| 9.801 | 5.8 |
| 14.061 | 19.5 |
| 15.365 | 10 |
| 16.515 | 11 |
| 18.379 | 7.7 |
| 19.319 | 7.5 |
| 20.778 | 34 |
| 22.888 | 11.1 |
| 23.794 | 10.3 |
| 25.016 | 11.2 |
| 25.931 | 6.5 |

Example 6

Preparation of the 1:1 (+)-(1S)-10-Camphorsulfonic Acid Salt of Stemospironine

Figure 7:
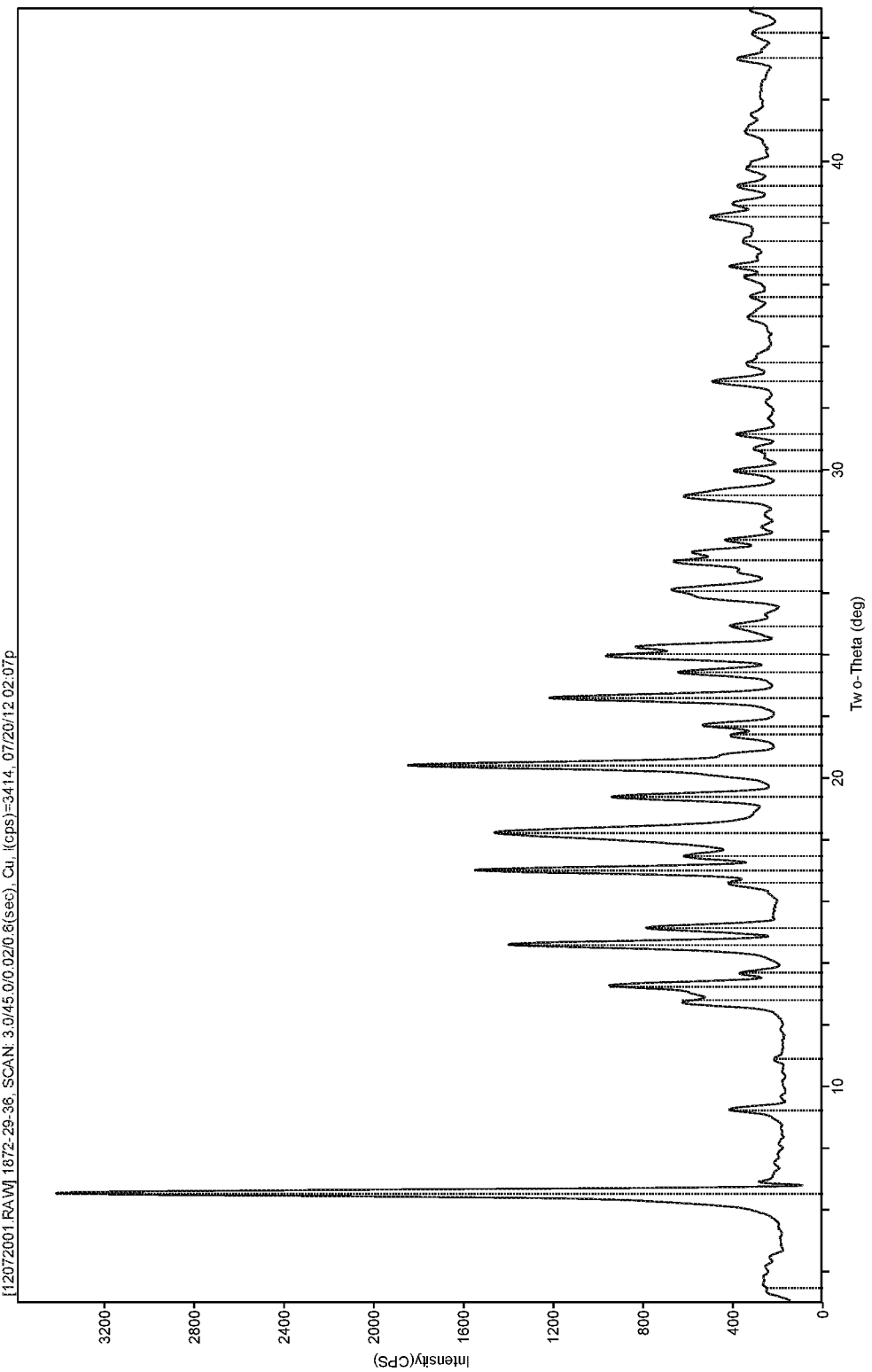
FIG. 7 shows a characteristic X-ray powder diffraction pattern of crystalline 1:1 (+)-(1S)-10-camphorsulfonic acid salt of stemospironine.

Using the method of Example 3 stemosporinnne and (+)-(1S)-10-camphorsulfonic acid, yielded the title compound as a crystalline solid which was characterized by) (RFD. FIG. 7 shows a characteristic X-ray powder diffraction (XRPD) pattern of the 1:1 (+)-(1S)-10-camphorsulfonic acid salt of stemospironine. Characteristic peaks, expressed in degrees 2θ, are listed in Table 7.

TABLE 7

| Angle 2θ [°] | Relative Intensity (%) |
|---|---|
| 6.519 | 100 |
| 9.225 | 7.5 |
| 12.798 | 11.9 |
| 13.237 | 23.4 |
| 13.696 | 3.3 |
| 14.586 | 36.9 |
| 15.136 | 17.7 |
| 17.005 | 37.1 |
| 17.474 | 5.8 |
| 18.221 | 35 |
| 19.393 | 20.9 |
| 20.411 | 50.1 |
| 21.673 | 9.8 |
| 22.6 | 30.9 |
| 23.431 | 12.3 |
| 24.022 | 22.7 |
| 26.059 | 13.1 |
| 27.062 | 12.5 |
| 29.172 | 12.2 |
| 32.865 | 7.9 |
| 38.199 | 7 |

Example 7

Preparation of the 1:1 Ethanesulfonic Acid Salt of Stemospironine

Figure 8:
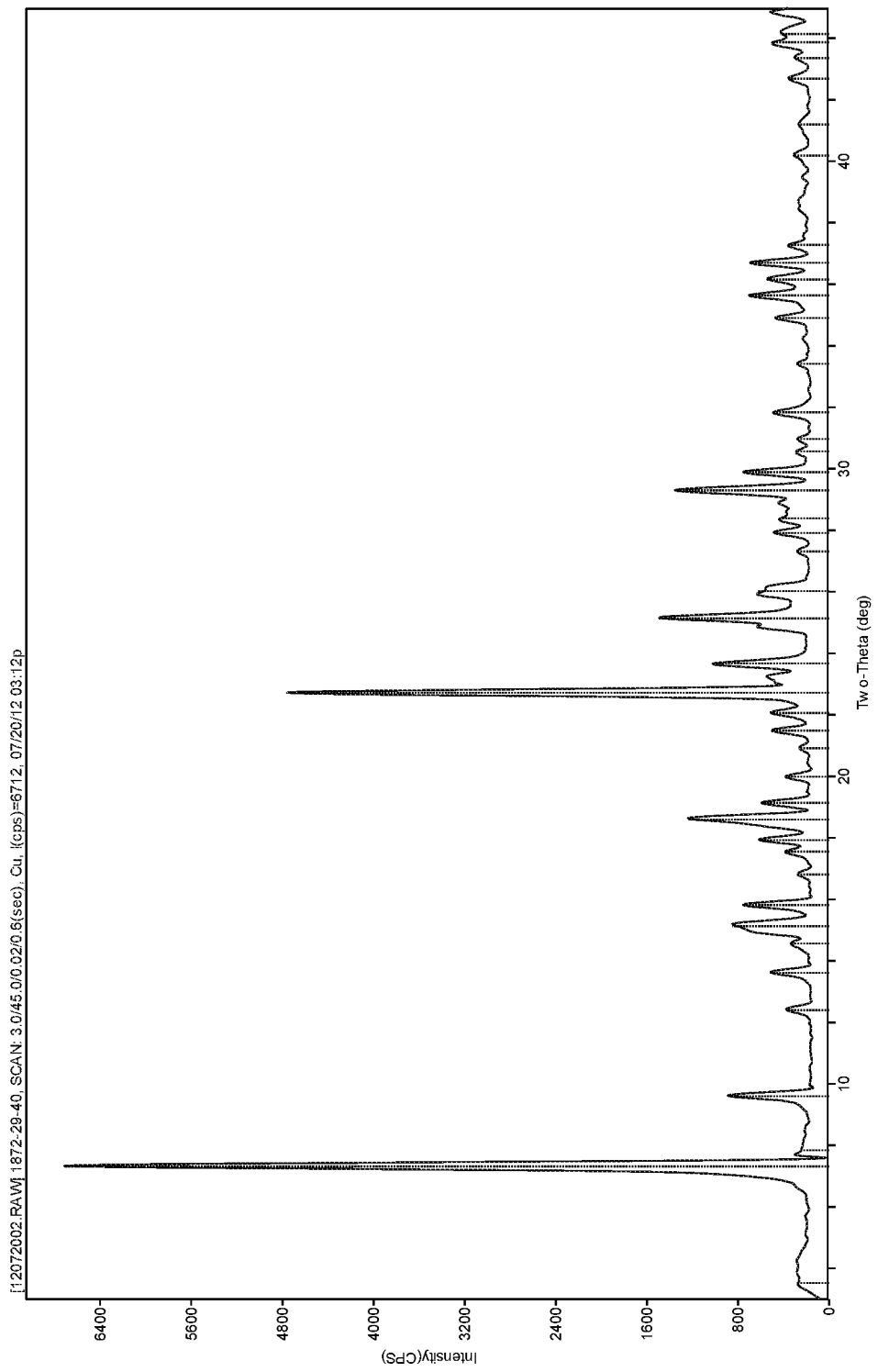
FIG. 8 shows a characteristic X-ray powder diffraction pattern of crystalline 1:1 ethanesulfonic acid salt of stemospironine.

Using the method of Example 3 stemosporinnne and ethanesulfonic acid yielded the title compound as a crystalline solid which was characterized by XRPD. FIG. 8 shows a characteristic X-ray powder diffraction (XRPD) pattern of the 1:1 ethanesulfonic acid salt of stemospironine. Characteristic peaks, expressed in degrees 2θ, are listed in Table 8.

TABLE 8

| Angle 2θ [°] | Relative Intensity (%) |
|---|---|
| 7.32 | 100 |
| 7.847 | 1.1 |
| 9.597 | 11.1 |
| 12.406 | 3.3 |
| 13.611 | 5.3 |
| 15.135 | 10.4 |
| 15.816 | 8.7 |
| 17.558 | 2.8 |
| 17.928 | 6.5 |
| 18.596 | 15.5 |
| 19.139 | 5.9 |
| 19.99 | 3.2 |
| 21.484 | 4.6 |
| 22.063 | 3.7 |
| 22.721 | 68.3 |
| 23.671 | 10.7 |
| 25.139 | 18.4 |
| 26.022 | 4.9 |
| 27.916 | 3.7 |
| 28.39 | 3.9 |
| 29.297 | 16 |
| 29.894 | 8.1 |
| 31.844 | 4.9 |
| 34.902 | 3.9 |
| 35.639 | 7.3 |
| 36.154 | 5.1 |
| 36.701 | 7.2 |
| 37.276 | 2.4 |

Example 8

Preparation of the 1:1 1,2-Ethanedisulfonic Acid Salt of Stemospironine

Figure 9:
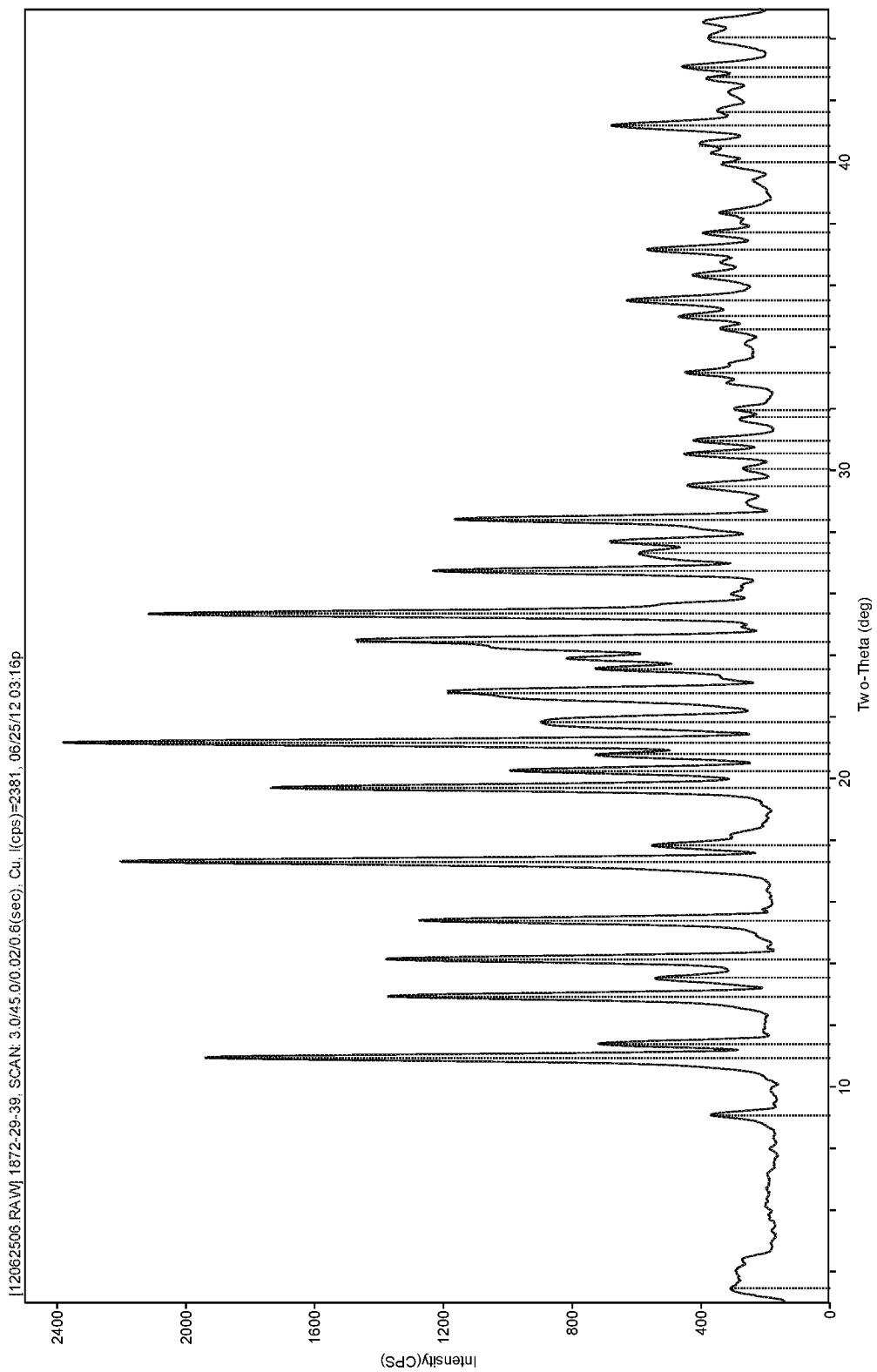
FIG. 9 shows a characteristic X-ray powder diffraction pattern of crystalline 1:1 1,2-ethanedisulfonic acid salt of stemospironine.

Using the method of Example 3 stemosporinnne and 1,2-ethanedisulfonic acid yielded the title compound as a crystalline solid which was characterized by XRPD. FIG. 9 shows a characteristic X-ray powder diffraction (XRPD) pattern of the 1:1 1,2-ethanedisulfonic acid salt of stemospironine. Characteristic peaks, expressed in degrees 2θ, are listed in Table 9.

TABLE 9

| Angle 2θ [°] | Relative Intensity (%) |
|---|---|
| 9.067 | 9.7 |
| 10.94 | 84.3 |
| 11.385 | 24.9 |
| 12.92 | 55 |
| 13.546 | 15.2 |
| 14.129 | 56.4 |
| 15.391 | 52.4 |
| 17.292 | 93.8 |
| 17.842 | 16.3 |
| 19.703 | 72.1 |
| 20.246 | 34.7 |
| 20.8 | 21.1 |
| 21.158 | 100 |
| 21.827 | 29.5 |
| 22.768 | 44.3 |
| 23.55 | 22.3 |
| 24.438 | 58.7 |
| 25.361 | 89.5 |
| 26.736 | 44.4 |
| 27.319 | 15.5 |
| 27.642 | 18.6 |
| 28.393 | 44.2 |
| 29.485 | 11.4 |
| 30.552 | 12.7 |
| 30.959 | 11.3 |
| 33.172 | 11.5 |
| 35.006 | 10.9 |
| 35.509 | 17.4 |
| 36.309 | 7 |
| 37.155 | 13.6 |
| 37.722 | 6.9 |
| 38.359 | 5.7 |
| 41.195 | 19 |

Example 9

Preparation of Crystalline Stemospironine Free Base

Figure 10:
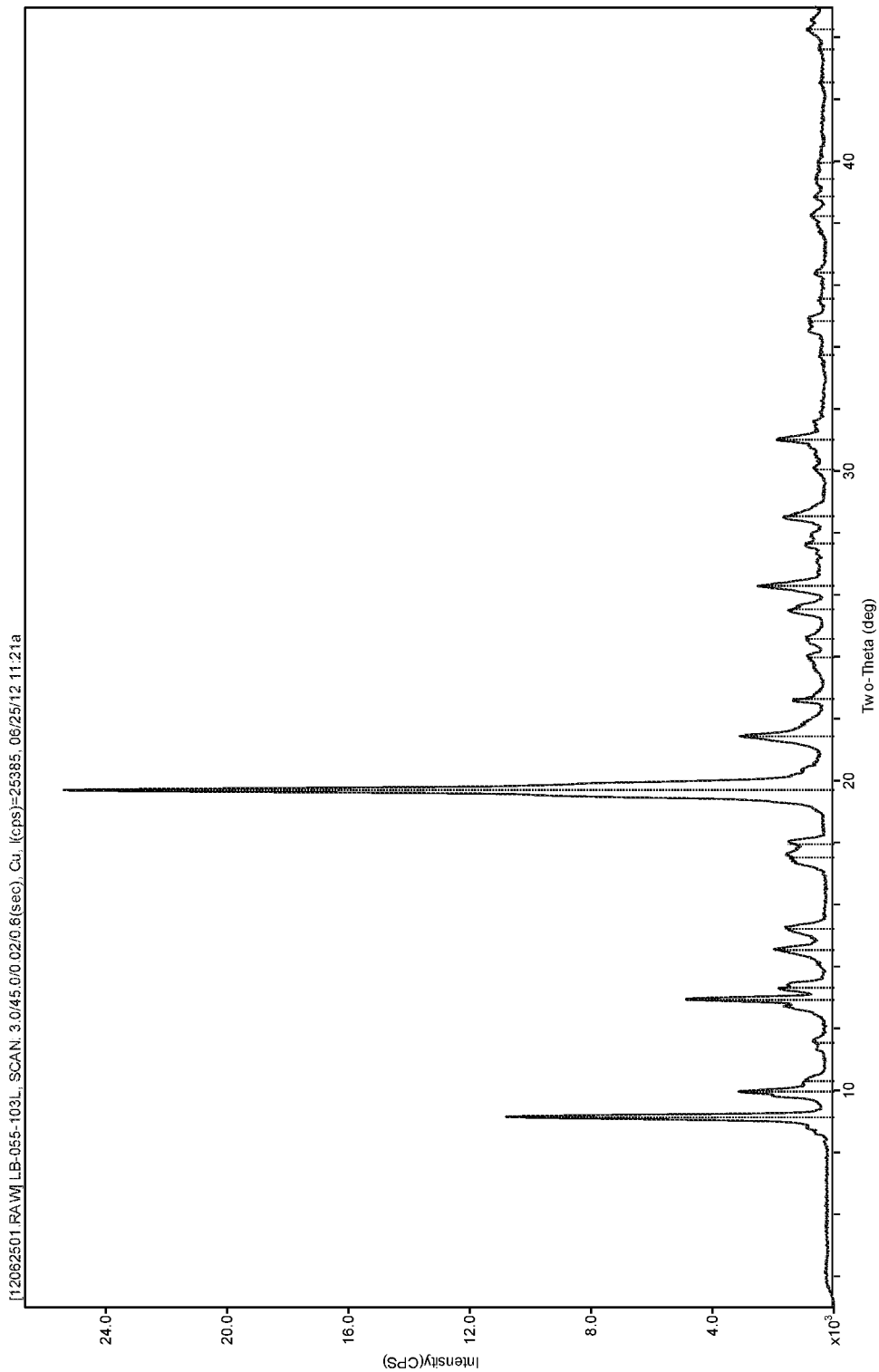
FIG. 10 shows a characteristic X-ray powder diffraction pattern of crystalline stemospironine.

Evaporation of an acetonitrile solution of the stemospironine free base at 25° C. afforded the title compound which was characterized by XRPD. FIG. 10 shows a characteristic X-ray powder diffraction (XRPD) pattern of crystalline stemosporinine. Characteristic peaks, expressed in degrees 2θ, are listed in Table 10.

TABLE 10

| Angle 2θ [°] | Relative Intensity (%) |
|---|---|
| 9.959 | 10.9 |
| 10.304 | 2.3 |
| 12.927 | 18.2 |
| 13.318 | 6 |
| 14.535 | 6.6 |
| 15.216 | 5.3 |
| 17.515 | 4.5 |
| 17.952 | 4.6 |
| 19.701 | 100 |
| 21.435 | 10.5 |

TABLE 10-continued

| Angle 2θ [°] | Relative Intensity (%) |
|---|---|
| 22.634 | 3.7 |
| 23.978 | 2 |
| 24.575 | 1.9 |
| 25.53 | 4.3 |
| 26.285 | 8.3 |
| 28.543 | 4.9 |
| 31.009 | 5.7 |

What is claimed is:

1. A crystalline stemospironine salt of Formula 1,

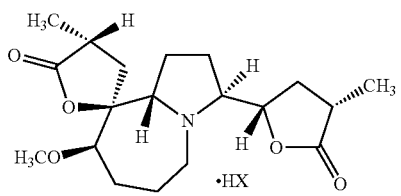

wherein HX is hydrogen chloride, in the form of a polymorph Form I that exhibits an X-ray powder diffraction pattern having at least the following 2θ reflection positions:

| 2θ |
|---|
| 8.818 |
| 9.333 |
| 13.806 |
| 14.065 |
| 14.853 |
| 15.568 |
| 15.931 |
| 17.514 |
| 18.621 |
| 18.966 |
| 20.494 |
| 22.731 |
| 24.228 |
| 25.159 |
| 26.217 |
| 27.697 |
| 28.455 |
| 29.167 |
| 30.124 |
| 32.384 |
| 33.101 |
| 33.584. |

2. A crystalline stemospironine salt of Formula 1,

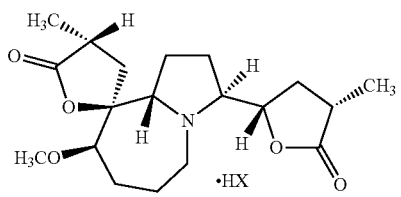

wherein HX is hydrogen chloride, in the form of a polymorph Form II that exhibits an X-ray powder diffraction pattern having at least the following 2θ reflection positions:

| 2θ |
|---|
| 8.772 |
| 9.294 |
| 13.795 |
| 14.137 |
| 14.825 |
| 15.47 |
| 15.889 |
| 17.456 |
| 18.579 |
| 22.702 |
| 23.047 |
| 24.39 |
| 25.128 |
| 25.593 |
| 26.174 |
| 27.929 |
| 28.389 |
| 29.153 |
| 29.993 |
| 32.39 |
| 33.083 |
| 33.55 |
| 36.186 |
| 37.594 |
| 39.215 |
| 39.851 |
| 42.139. |

3. A crystalline stemospironine salt of Formula 1,

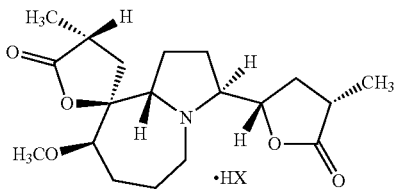

wherein HX is hydrogen bromide, that exhibits an X-ray powder diffraction pattern having at least the following 2θ reflection positions:

| 2θ |
|---|
| 8.664 |
| 9.434 |
| 13.648 |
| 14.179 |
| 15.188 |
| 15.84 |
| 17.588 |
| 20.174 |
| 21.559 |
| 22.755 |
| 23.644 |
| 24.567 |
| 25.924 |
| 26.445 |
| 27.666 |
| 27.949 |
| 28.827 |
| 29.306 |
| 30.268 |
| 31.1 |
| 32.198 |
| 33.95 |
| 36.298 |
| 42.236. |

4. A crystalline stemospironine salt of Formula 1,

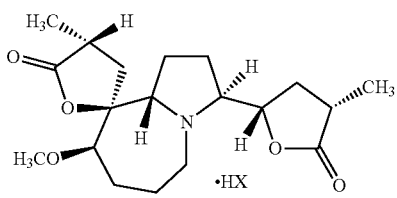

wherein HX is L-tartaric acid, that exhibits an X-ray powder diffraction pattern having at least the following 2θ reflection positions:

| 2θ |
| --- |
| 10.873 |
| 12.296 |
| 14.346 |
| 15.269 |
| 16.703 |
| 17.363 |
| 18.277 |
| 18.979 |
| 19.871 |
| 20.409 |
| 22.259 |
| 23.388 |
| 24.589 |
| 25.362 |
| 26.002 |
| 26.96 |
| 27.551 |
| 28.973 |
| 29.758 |
| 30.31 |
| 31.063 |
| 31.914 |
| 35.009 |
| 35.603 |
| 36.677 |
| 37.476 |
| 38.172 |
| 38.918 |
| 39.497 |
| 40.682 |
| 41.781. |

5. A crystalline stemospironine salt of Formula 1,

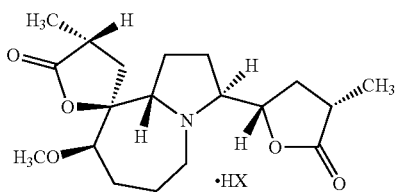

wherein HX is D-tartaric acid, that exhibits an X-ray powder diffraction pattern having at least the following 2θ reflection positions:

| 2θ |
| --- |
| 9.834 |
| 11.641 |
| 12.342 |
| 13.487 |
| 14.967 |
| 15.957 |
| 17.457 |
| 18.57 |
| 19.583 |
| 20.583 |
| 21.63 |
| 22.655 |
| 24.738 |
| 25.312 |
| 27.084 |
| 27.63 |
| 29.432 |
| 30.163 |
| 31.035 |
| 34.582 |
| 35.16 |
| 36.489 |
| 38.156 |
| 40.849 |
| 41.401. |

6. A crystalline stemospironine salt of Formula 1,

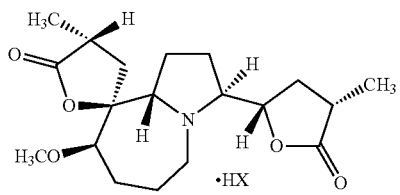

wherein HX is sulfuric acid, that exhibits an X-ray powder diffraction pattern having at least the following 2θ reflection positions:

| 2θ |
| --- |
| 7.13 |
| 9.257 |
| 9.801 |
| 14.061 |
| 15.365 |
| 16.515 |
| 18.379 |
| 19.319 |
| 20.778 |
| 22.888 |
| 23.794 |
| 25.016 |
| 25.931. |

7. A crystalline stemospironine salt of Formula 1,

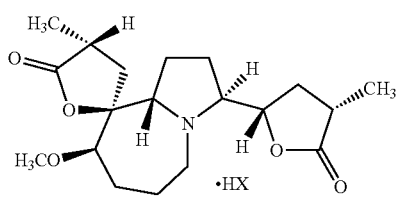

wherein HX is (+)-(1S)-10-camphorsulfonic acid, that exhibits an X-ray powder diffraction pattern having at least the following 2θ reflection positions:

| 2θ |
|---|
| 6.519 |
| 9.225 |
| 12.798 |
| 13.237 |
| 13.696 |
| 14.586 |
| 15.136 |
| 17.005 |
| 17.474 |
| 18.221 |
| 19.393 |
| 20.411 |
| 21.673 |
| 22.6 |
| 23.431 |
| 24.022 |
| 26.059 |
| 27.062 |
| 29.172 |
| 32.865 |
| 38.199. |

8. A crystalline stemospironine salt of Formula 1,

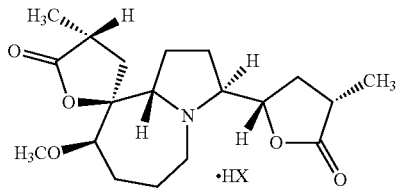

wherein HX is ethanesulfonic acid, that exhibits an X-ray powder diffraction pattern having at least the following 2θ reflection positions:

| 2θ |
|---|
| 7.32 |
| 7.847 |
| 9.597 |
| 12.406 |
| 13.611 |
| 15.135 |
| 15.816 |
| 17.558 |
| 17.928 |
| 18.596 |
| 19.139 |
| 19.99 |
| 21.484 |
| 22.063 |
| 22.721 |
| 23.671 |
| 25.139 |
| 26.022 |
| 27.916 |
| 28.39 |
| 29.297 |
| 29.894 |
| 31.844 |
| 34.902 |
| 35.639 |
| 36.154 |
| 36.701 |
| 37.276. |

9. A crystalline stemospironine salt of Formula 1,

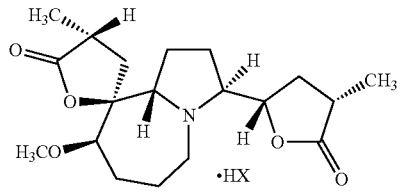

wherein HX is 1,2-ethanedisulfonic acid, that exhibits an X-ray powder diffraction pattern having at least the following 2θ reflection positions:

| 2θ |
|---|
| 9.067 |
| 10.94 |
| 11.385 |
| 12.92 |
| 13.546 |
| 14.129 |
| 15.391 |
| 17.292 |
| 17.842 |
| 19.703 |
| 20.246 |
| 20.8 |
| 21.158 |
| 21.827 |
| 22.768 |
| 23.55 |
| 24.438 |
| 25.361 |
| 26.736 |
| 27.319 |
| 27.642 |
| 28.393 |
| 29.485 |
| 30.552 |
| 30.959 |
| 33.172 |
| 35.006 |
| 35.509 |
| 36.309 |
| 37.155 |
| 37.722 |
| 38.359 |
| 41.195. |

10. A crystalline form of the compound of Formula 2, stemospironine free base,

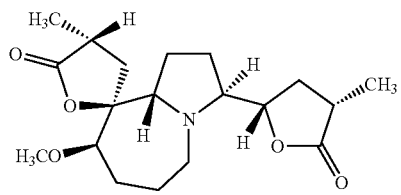

that exhibits an X-ray powder diffraction pattern having at least the following 2θ reflection positions:

| 2θ |
|---|
| 9.959 |
| 10.304 |
| 12.927 |
| 13.318 |
| 14.535 |
| 15.216 |
| 17.515 |
| 17.952 |
| 19.701 |
| 21.435 |
| 22.634 |
| 23.978 |
| 24.575 |
| 25.53 |
| 26.285 |
| 28.543 |
| 31.009. |

11. A pharmaceutical composition comprising one or more compounds of claim 1 and a pharmaceutically acceptable carrier.

12. A pharmaceutical composition comprising one or more compounds of claim 2 and a pharmaceutically acceptable carrier.

13. A pharmaceutical composition comprising one or more compounds of claim 3 and a pharmaceutically acceptable carrier.

14. A pharmaceutical composition comprising one or more compounds of claim 4 and a pharmaceutically acceptable carrier.

15. A pharmaceutical composition comprising one or more compounds of claim 5 and a pharmaceutically acceptable carrier.

16. A pharmaceutical composition comprising one or more compounds of claim 6 and a pharmaceutically acceptable carrier.

17. A pharmaceutical composition comprising one or more compounds of claim 7 and a pharmaceutically acceptable carrier.

18. A pharmaceutical composition comprising one or more compounds of claim 8 and a pharmaceutically acceptable carrier.

19. A pharmaceutical composition comprising one or more compounds of claim 9 and a pharmaceutically acceptable carrier.

20. A pharmaceutical composition comprising one or more compounds of claim 10 and a pharmaceutically acceptable carrier.

* * * * *